United States Patent [19]

Mauvernay et al.

[11] 4,086,352
[45] Apr. 25, 1978

[54] CERTAIN 6-ARYLOXY-2-OXO-1-AZA-4-THIA-SPIRO[4,5]DECANES

[75] Inventors: Roland Yves Mauvernay, Riom; Norbert Busch, La Tourette; Jacques Moleyre, Menetrol; Jacques Simond, Chamalieres; André Monteil, Gerzat, all of France

[73] Assignee: Centre Europeen de Recherches Mauvernay, Riom, France

[21] Appl. No.: 717,716

[22] Filed: Aug. 25, 1970

Related U.S. Application Data

[62] Division of Ser. No. 616,357, Sep. 24, 1975, Pat. No. 4,000,292.

[30] Foreign Application Priority Data

Sep. 27, 1974  France ........................ 74 32777
Aug. 4, 1975  France ........................ 75 24296

[51] Int. Cl.² ................. A61K 31/425; C07D 277/14
[52] U.S. Cl. ........................ 424/270; 260/306.7 R
[58] Field of Search ............... 260/306.7 R; 424/270

[56] References Cited

U.S. PATENT DOCUMENTS 4,000,292  12/1976  Mauvernay et al. ........ 260/306.7 R

Primary Examiner—Richard J. Gallagher
Attorney, Agent, or Firm—Burgess, Dinklage & Sprung

[57] ABSTRACT

The invention relates to novel 6-aryloxy-2-oxo-1-aza-4-(or thia)-spiro[4,5]decane compounds. These compounds are represented by the formula:

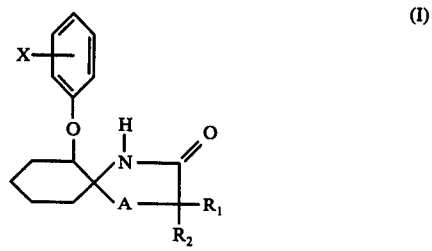

(I)

in which A stands for an oxygen or sulfur heteroatom; $R_1$ and $R_2$ are each H, lower alkyl or aryl such as phenyl; X is H, a halogen atom such as chlorine or fluorine or a lower alkyl.

Compounds according to the invention are useful as stimulating agents for vigilance, as psycho-stimulators and genesic stimulators.

6 Claims, No Drawings

CERTAIN 6-ARYLOXY-2-OXO-1-AZA-4-THIA-SPIRO[4,5]-DECANES

This is a division of application Ser. No. 616,357, filed Sept. 24, 1975, now U.S. Pat. No. 4,000,292, issued Dec. 28, 1976.

This invention relates to novel 6-aryloxy-2-oxo-1-aza-4-oxa (or thia)-spiro[4,5]decane compounds and to a method for the production thereof. A further object of the invention resides in the application of said compounds as medicines, in particular as stimulating agents, especially for the central nervous system or psychotonic agents.

Pharmaceutical compositions containing, as active ingredient, at least one compound of the invention are also included within the scope of this invention.

There are already known chemical compounds having stimulating properties for the central nervous system (see for example J. BICKING et al., J. Med. Chim. 8,95 (1965).

L. SCHMITT (Arzneimittel Forsch. 6,423 (1956) has brought into light the stimulating properties for the central nervous system achieved by means of 2-imino-5-phenyl-4-oxazolidinone.

Furthermore, Japanese patent application No.7,225,355 in the name of Yoshitomi filed July 11, 1972, discloses a process for obtaining compounds of the general formula:

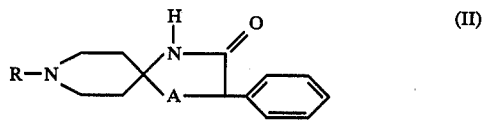

useful as depressants of the central nervous system and as hypoglycemic agents.

Another product which may be cited as a stimulator of the central nervous system and of the sympathetic system is the Amphetamine (or methyl-phenetylamine).

There have now been found new compounds having a structure different from that of the above mentioned compounds and possessing stimulating properties for the central nervous system. The compounds which are the subject matter of the invention are the 6-aryloxy-2-oxo-1-aza-4-oxa(or thia)-spiro[4,5]decanes of the general formula (I)

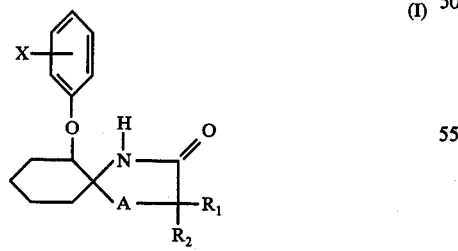

in which A stands for an oxygen or sulfur heteroatom; $R_1$ and $R_2$ each represent, independently from one another, hydrogen, lower alkyl or aryl such as phenyl; X is hydrogen, a halogen atom, such as chlorine or fluorine, or a lower alkyl.

Another object of the invention is a method for obtaining the 6-aryloxy-2-oxo-1-aza-4-oxa(or thia)-spiro[4,5]decanes of formula I hereabove. The process of the invention comprises condensing, in an aromatic solvent and in the presence of an ammonium salt and a dehydrating catalyst, substantially equimolar amounts of 2-phenoxy-cyclohexanone and an acid of formula:

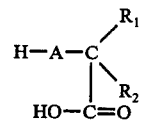

in which A, $R_1$ and $R_2$ have the same meanings as hereabove, the condensation being effected by heating to reflux until the theoretical amount of formed water is entirely collected by means of the azeotrope formed with a solvent.

In accordance with the invention, the reaction is effected in an aromatic solvent such as benzene, toluene or xylene; the ammonium salt is advantageously ammonium carbonate, and the dehydrating catalyst can be for example p-toluene-sulfonic acid.

The 2-phenoxy-cyclohexanone used in the process of the invention must be substituted on the phenoxy group by a suitable radical X, the latter having the meaning aforesaid.

The 2-phenoxy-cyclohexanone employed in the process of the invention may be obtained, for example, from substantially equimolar amounts of a suitably substituted phenol and 2-chloro-cyclohexanone by heating to reflux the solvent in the presence of potassium carbonate in acetone medium.

Accordingly, the process of the invention, considered as a whole, can be illustrated for instance by the following reaction sequence:

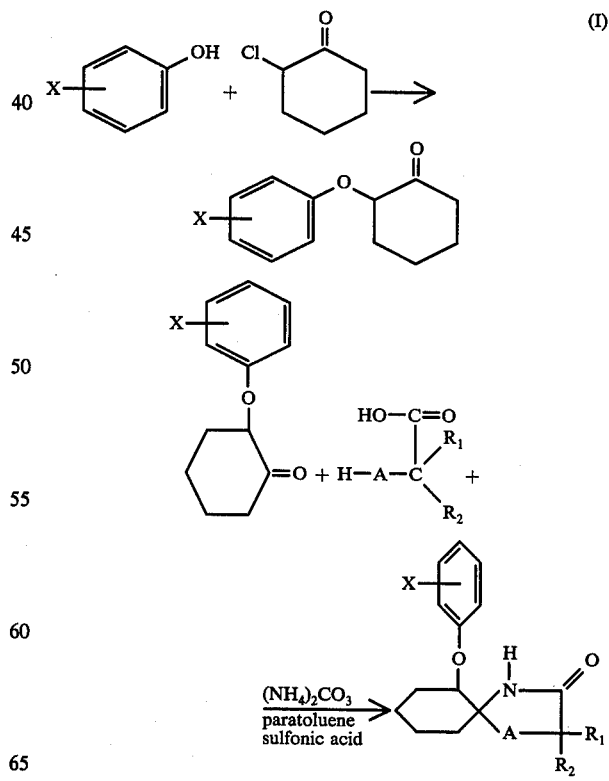

As already mentioned, the compounds of the invention are useful as medicines for the central nervous system, as stimulators or psychotonic agents. Certain pharmacological properties of the compounds of the invention allow them to be considered as close to no-analeptics. Generally, they are useful in human therapeutics as stimulators of vigilance, psychostimulators and genesic stimulators.

The toxicity of the compounds according to the invention is substantially lower than that of the Amphetamine (or methylphenethylamine); it should be noted in this respect that at a dose of 300 mg/kg administered orally to the mouse, no death is observed when using compounds of the invention, whereas the same dosage of Amphetamine causes 100% death of mice.

The compounds of the invention can be used in the form of pharamaceutical preparations to be administered to the human, orally at a dosage of 25 to 150 mg./day or parenterally.

The invention will be illustrated in more detail by the following non limiting examples.

EXAMPLE 1

Synthesis of 6-(4-fluoro)phenoxy-3,3-dimethyl-2-oxo-1-aza-4-oxa-spiro[4,5]decane(compound No. 8) Preparation of 2-(4-fluoro)phenoxy-cyclohexane-1-one Into a reactor there were introduced 0.5 mole (56 g) of 4-fluoro-phenol, 0.485 mole (63.5 g) of 2-chloro-cyclohexanone and 45 g of potassium carbonate in 150 ml of acetone. The mixture was refluxed 30 hours.

After filtering the reaction mixture, the solution was concentrated to dryness and the residue washed with a 10% solution of soda and then with water.

There was thus obtained 57 g of 2-(4-fluoro-)phenoxy-cyclohexane-1-one, the melting point of which was 78° C.

Condensation of the above cyclohexanone with 2-hydroxyiso-butyric acid

In a three-necked flask provided with refrigeration, central stirring and an azeotropic tube, there was refluxed a mixture consisting of 0.1 mole (20.8 g) of the previously prepared cyclohexanone, 0.12 mole (12.48 g) of α-hydroxy-isobutyric acid, 13.1 g of ammonium carbonate and 0.5 g of p-toluene sulfonic acid in 180 ml of toluene.

After separation of the theoretical amount of water, the toluene solution was washed with water, then with soda diluted to 10% and again with water. The toluene solution was concentrated under vacuum.

The obtained residue has been crystallized from isopropanol. After recrystallization in isopropanol, there was obtained about 15 g of the title compound having a melting point of 205° C. The results of the elemental analysis of the thus-obtained product are given in table I hereunder.

EXAMPLE 2

Synthesis of 6-(4-methyl)phenoxy-3-methyl-2-oxo-1-aza-4-thia-spiro[4,5]decane(compound No. 10). Preparation of 2-(4-methyl)-phenoxy cyclohexane-1-one The steps described in Example 1 were repeated, using 54 g (0.5 M) of p-cresol, 63.5 g (0.485 M) of 2-chloro-cyclohexanone and 45 g of potassium carbonate in 150 ml of acetone; there was obtained 40 g of a product having a melting point of 89° C.

Condensation of cyclohexanone prepared hereabove with 2-mercaptopropionic acid.

Using 20.2 g of the cyclohexanone prepared in the immediately preceding step, 12.72 g of 2-mercaptopropionic acid, 13.1 g of ammonium carbonate and 0.5 g of p-toluene sulfonic acid, there was obtained by the same method as in example 1.12 g of the title compound having a melting point of 194° C. The results of the elemental analysis of the thus obtained product are given in table I hereunder.

EXAMPLE 3

Synthesis of 6-(3-chloro)phenoxy-3-methyl-2-oxo-1-aza-4-thia-spiro[4,5]decane(compound No. 14). Preparation of 2-(3-chloro)phenoxy cyclohexane 1-one Into a reactor, there were introduced 1 mole (128.5 g) of 3-chlorophenol, 0.97 mole (127 g) of 2-chloro-cyclohexanone and 90 g of potassium carbonate in 300 ml of acetone. The mixture was refluxed for 4 days.

After filtering the reaction mixture, the solution was concentrated to dryness and the residue has been washed with a 10% soda solution, then with water until complete removal of residual phenol, the purification being monitored by I.R.-chromatography.

There was thus obtained 112 g of 2-(4-fluoro-phenoxy cyclohexane)-1-one.

Condensation of cyclohexanone hereabove with thiolactic acid

Into a reactor of 500 ml capacity provided with an azeotropic tube, there were introduced 0.1 mole (22.45 g) of the cyclohexanone obtained in the preceding step, 0.12 ml (12.72 g) of thiolactic acid, 13.1 g of ammonium carbonate and 0.5 g of p-toluene sulfonic acid, using as solvent 180 ml of toluene.

The mixture was refluxed 15 hours while removing the water being formed. The mixture was concentrated under vacuum and taken in 400 ml of chloroform. The solution was washed with water, with soda diluted to 10% and again with water.

After drying of sodium sulfate, the chloroform solution was concentrated under vacuum and the product crystallized in isopropanol.

After recrystallization in isopropanol, there was obtained 15 g of the product, which had a melting point of 131° C and corresponded to the elemental analysis given in table I hereinbelow.

EXAMPLE 4

Synthesis of 6-(4-chloro)phenoxy-3-phenyl-2-oxo-1-aza-4-oxa-spiro[4,5]decane(compound No. 15)

Operating as in example 3, but replacing the 3-chloro-phenol by the 4-chlorophenol and with heating to reflux 3 days, there was obtained in a first stage 165 g of 2-(4-chloro)phenoxy-cyclohexane-1-one.

In a second stage, there was condensed 0.1 mole (22.45 g) of the previously obtained cyclohexanone with 0.12 mole (18.25 g) of mandelic acid in the presence of 13.1 g of ammonium carbonate and 1 g of p-toluene sulfonic acid in 180 ml toluene.

After elimination of the theoretical amount of water, successive washings with a 10% soda solution and with water, followed by recrystallization in isopropanol, there was obtained the title product, the melting point of which, determined by means of a Maquenne Block, was 190° C and the elemental analysis of which was as indicated in Table I.

EXAMPLE 5

The operations disclosed in Examples 1 to 4 have been repeated using, as 2-phenoxycyclohexanone, one of the following compounds:
2-(3-methyl)-phenoxy-cyclohexane-1-one
2-(3-chloro)-phenoxy-cyclohexane-1-one
2-(4-methyl)-phenoxy-cyclohexane-1-one
2-(4-fluoro)-phenoxy-cyclohexane-1-one
2-(2-methyl)-phenoxy-cyclohexane-1-one
2-phenoxy-cyclohexanone
2-(4-chloro)phenoxy-cyclohexane-1-one.
and as acids, one of the following:
2-hydroxy-propionic acid
2-hydroxy-2-phenyl-ethanoic acid
α-hydroxy-isobutyric acid, and
2-mercapto-propionic acid.
to thus obtain the compounds the features of which are presented in Table I hereunder (the substituents being those respectively mentioned in columns A, $R_1$, $R_2$ and X of said Table). Said compounds are respectively:
6-(3-methyl)phenoxy-3-methyl-2-oxo-1-aza-4-oxa-spiro[4,5]decane
6-(3-methyl)phenoxy-3-phenyl-2-oxo-1-aza-4-oxa-spiro[4,5]decane
6-(3-chloro)phenoxy-3-phenyl-2-oxo-1-aza-4-oxa-spiro[4,5]decane
6-(3-chloro)phenoxy-3-methyl-2-oxo-1-aza-4-oxa-spiro[4,5]decane
6-(4-methyl)phenoxy-3-methyl-2-oxo-1-aza-4-oxa-spiro[4,5]decane
6-(4-methyl)phenoxy-3,3-dimethyl-2-oxo-1-aza-4-oxa-spiro[4,5]decane
6-(3-methyl)phenoxy-3,3-dimethyl-2-oxo-1-aza-4-oxa-spiro[4,5]decane
6-(4-fluoro)phenoxy-3-methyl-2-oxo-1-aza-4-oxa-spiro[4,5]decane
6-phenoxy-3-methyl-2-oxo-1-aza-4-thia-spiro[4,5]decane
6-(2-methyl)phenoxy-3-methyl-2-oxo-1-aza-4-thia-spiro[4,5]decane,
and 6-(3-methyl)phenoxy-3-methyl-2-oxo-1-aza-4-thia-spiro[4,5]decane.

TABLE I

| compound no | A | $R_1$ | $R_2$ | X | molecular weight | melting point | C % | H % | N % |
|---|---|---|---|---|---|---|---|---|---|
| 1 | O | H | —CH₃ | m-CH₃ | 275.35 | 175° C | th 69.79 | 7.69 | 5.09 |
|   |   |   |   |   |   |   | F 71.37 | 7.55 | 4.93 |
| 2 | O | H | ⌬ (phenyl) | m-CH₃ | 337.4 | 220° C | th 74.7 | 6.87 | 4.15 |
|   |   |   |   |   |   |   | F 75.16 | 7.14 | 4.16 |
| 3 | O | H | ⌬ (phenyl) | m-Cl | 357.8 | 211° C | th 67.13 | 5.63 | 3.91 |
|   |   |   |   |   |   |   | F 68.34 | 5.91 | 4.04 |
| 4 | O | H | —CH₃ | m-Cl | 295.8 | 163° C | th 60.91 | 6.13 | 4.73 |
|   |   |   |   |   |   |   | F 61.02 | 6.08 | 4.76 |
| 5 | O | H | —CH₃ | p-CH₃ | 275.35 | 203° C | th 69.79 | 7.69 | 5.09 |
|   |   |   |   |   |   |   | F 70.18 | 7.84 | 5.01 |
| 6 | O | —CH₃ | —CH₃ | p-CH₃ | 289.4 | 226° C | th 70.56 | 8.01 | 4.84 |
|   |   |   |   |   |   |   | F 71.16 | 8.47 | 4.72 |
| 7 | O | —CH₃ | —CH₃ | m-CH₃ | 289.4 | 175° C | th 70.56 | 8.01 | 4.84 |
|   |   |   |   |   |   |   | F 72.16 | 7.76 | 4.70 |
| 8 (ex.1) | O | —CH₃ | —CH₃ | p-F | 293.34 | 205° C | th 65.51 | 6.87 | 4.77 |
|   |   |   |   |   |   |   | F 66.11 | 7.17 | 4.67 |
| 9 | O | H | —CH₃ | p-F | 279.32 | 138° C | th 64.50 | 6.49 | 5.20 |
|   |   |   |   |   |   |   | F 65.12 | 6.83 | 5.10 |
| 10 (ex.2) | S | H | —CH₃ | p-CH₃ | 291.42 | 194° C | th 65.94 | 7.26 | 4.80 |
|   |   |   |   |   |   |   | F 64.92 | 7.57 | 4.84 |
| 11 | S | H | —CH₃ | H | 277.4 | 135° C | th 64.95 | 6.90 | 5.05 |
|   |   |   |   |   |   |   | F 65.13 | 7.13 | 4.98 |
| 12 | S | H | —CH₃ | O—CH₃ | 291.42 | 165° C | th 65.94 | 7.26 | 4.80 |
|   |   |   |   |   |   |   | F 65.48 | 7.12 | 4.77 |
| 13 | S | H | —CH₃ | m-CH₃ | 291.42 | 130° C | th 65.94 | 7.26 | 4.80 |
|   |   |   |   |   |   |   | F 65.80 | 7.38 | 4.70 |
| 14 (ex 3) | S | —H | —CH₃ | m-Cl | 315,84 | 131° C | th. 57,04 | 5,74 | 4,43 |
|   |   |   |   |   |   |   | T. 57,50 | 5,69 | 4,38 |
| 15 (ex 4) | O | —H | ⌬ (phenyl) | p.Cl | 357,84 | 190° C | th. 67,12 | 5,63 | 3,91 |
|   |   |   |   |   |   |   | T. 68,20 | 5,64 | 4,02 |
| 16 | S | —H | —CH₃ | p.Cl | 315,84 | 152° C | th. 57,04 | 5,74 | 4,43 |
|   |   |   |   |   |   |   | T. 57,49 | 5,55 | 4,38 |
| 17 | O | —CH₃ | —CH₃ | p.Cl | 309,8 | 175° C | th. 62,03 | 6,50 | 4,52 |
|   |   |   |   |   |   |   | T. 62,85 | 6,30 | 4,51 |
| 18 | O | —H | —CH₃ | —H | 261,32 | 224° C | th. 68,94 | 7,93 | 5,36 |
|   |   |   |   |   |   |   | T. 70,44 | 7,40 | 5,32 |
| 19 | O | —CH₃ | —CH₃ | m-Cl | 309,8 | 198° C | th. 62,03 | 6,50 | 4,52 |
|   |   |   |   |   |   |   | T. 62,78 | 6,50 | 4,53 |
| 20 | O | —H | —CH₃ | p.Cl | 295,8 | 162° C | th. 60,91 | 6,13 | 4,73 |

TABLE I-continued

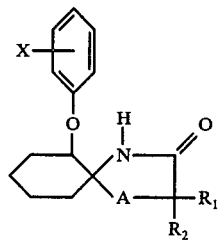

| compound no | A | $R_1$ | $R_2$ | X | molecular weight | melting point | C % | H % | N % |
|---|---|---|---|---|---|---|---|---|---|
| | | | | | | | T. 61,50 | 5,98 | 4,60 |

Various conventional tests effected on the central nervous system, as disclosed in the following examples, have brought to light the pharmacological activity of the compounds of the invention.

Pharmacological study

Acute toxicity

This has been determined on the mouse by oesophagian intubation of the tested compounds suspended in labrafil. The symptomatology of intoxication has been observed during the first 2 hours and then daily during 2 days: no death was observed at a dosage > 200 mg/kg.

Spontaneous motility of the mouse (in ambient atmosphere and in an atmosphere with lower oxygen level).

The spontaneous motility of the mouse has been studied by means of a circular corridor swept by infra-red beams enabling the number of trips effected by the mouse to be measured. A first batch of mice have received orally a compound according to the invention, the administered amount per body weight (kg) of each mouse being shown in table II hereunder, and there has been measured the percentage of variations of the number of trips effected by the mice in the circular corridor after the administration of the compound according to the invention.

It should be noted that the compound numbers 4, 9, 11 and 14 have caused a substantial motorial excitation of the mouse, which persisted in an atmosphere of lower oxygen content. The motility test in an atmosphere poor in oxygen has been effected by the same technique as thereabove, but with progressive introduction of nitrogen through the ceiling of the enclosure. The activity of the product used in this test leads to the assumption that the product of the invention shall not have any noxious effect even in cases of difficult brain oxygenation.

Food consumption

This test suggested by POSCHEL B.P.H. "A simple specific screen for benzodiazepine like drugs" Psychopharmacologia (Berl) 19, 193–198 (1971) comprises presenting to non-thirsty, non-hungry simple-minded rats feeding bottles based on condensed milk. This unusual beverage causes a reduction of the consumption; after administration of the compound under study, there is noted the number and average duration of the consumption test and the consumed volume, by comparing said results to those obtained with a control group. An increase of the consumption is interpreted as a deinhibition of the natural aversion of the rat for food to which it is not accustomed.

The pharmacological results are given in table II hereinafter.

TABLE II

| Compound No | Spontaneous motility | Motility in air poor in oxygen | Poschel test |
|---|---|---|---|
| 3 | 100;+10% | | |
| 4 | 25;+49% | 25;active | 50;inactive* |
| 5 | 100;−17% | 100;inactive | 50;inactive* |
| 8 | 25;+13% | | |
| 9 | 100;+60% | 100;active | 25;inactive* |
| 10 | 100;+21% | 100;active | 50;increase |
| 11 | 100;+66% | 100;active | 50;increase |
| 14 | 25;+41% | 25;very active | 25;increase |
| 15 | 100;+ 8% | 100;active | 25;increase |
| 16 | 100;+13% | 100;inactive | 50;inactive* |
| 17 | 100;+35% | 100;inactive | 25;inactive* |
| 18 | 100;+43% | 100;inactive | 50;increase |
| 19 | 100;+17% | 100;active | 50;increase |
| 20 | 100;+38% | 100;active | 25;increase |

*"inactive" means that the administration of the product according to the invention leads neither to an increase nor above all to a decrease of the food composition.

On the other hand the behavior test according to IRWIN [Nodine J. H. Siegler P. E. Year Book publ. (4) 36–54, 1963] effected on mice has further demonstrated hyperreactivity upon manipulations, hyperthermic and exophtalmic manifestations, as well as a certain genesic excitation, which was apparently unknown heretofore with the no-analeptic compounds.

There also has been noted that the compounds gave a negative or a non significant response in the test of supramaximum electroshock [PUTNAM T. J. MEERITT H. H. Science 85, 525–26 (1937)], the oxotremorine test [EVERETT G. M. BLOCKUS L. E., SHEPPERD I. M. Science 124, 79 (1956)], and the analgesic test by means of heating plate [EDDY N. B. LEIMBACH D. Synthetic analgesics II dithienyl and dithyenyl butylamines J. Pharmacol. Exp. Ther., 107 385–393 (1953)].

Thus, the disclosed compounds can be considered pharmacologically as exciting agents for the central nervous system but, contrary to Amphetamine, they remain inactive in the three described tests and, in opposition to the latter product, they even stimulate food consumption.

Accordingly the compounds of the invention are useful in therapeutics as psychotonic agents, administered in usual pharmaceutical-preparations forms, e.g., in tablets each containing 25 mg of active material.

It is to be understood that the foregoing description has been made solely by way of an illustration, without any intent to limit the invention, which is defined only by the appended claims.

What we claim is:

1. A compound of the formula

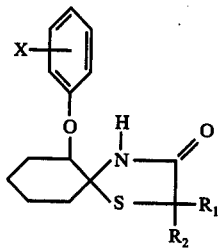

(I)

in which
R₁ is hydrogen or methyl,
R₂ is hydrogen, methyl or phenyl, and
X is hydrogen, a halogen atom or methyl.

2. A compound according to claim 1, wherein R₂ represents a phenyl group.

3. A compound according to claim 1, wherein X is chlorine or fluorine.

4. A compound according to claim 1, which is selected from amongst the following compounds:

6-(4-methyl)phenoxy-3-methyl-2-oxo-1-aza-4-thia-spiro[4,5]decane,
6-phenoxy-3-methyl-2-oxo-1-aza-4-thia-spiro[4,5]decane,
6-(2-methyl)-phenoxy-3-methyl-2-oxo-1-aza-4-thia-spiro[4,5]decane,
6-(3-methyl)phenoxy-3-methyl-2-oxo-1-aza-4-thia-spiro[4,5]decane,
6-(3-chloro)phenoxy-3-methyl-2-oxo-1-aza-4-thia-spiro[4,5]decane, and
6-(4-chloro)phenoxy-3-methyl-2-oxo-1-aza-4-thia-spiro[4,5]decane.

5. A central nervous system stimulating composition, which comprises, as active ingredient, an amount of a compound as defined in claim 1 sufficient to stimulate the central nervous system, in combination with a pharmaceutically acceptable vehicle.

6. A method for stimulating the central nervous system which comprises administering to the patient an amount of a compound as described in claim 1 sufficient to stimulate the central nervous system.

* * * * *

UNITED STATES PATENT AND TRADEMARK OFFICE
CERTIFICATE OF CORRECTION

PATENT NO. : 4,086,352
DATED : April 25, 1978
INVENTOR(S) : Roland Yves Mauvernay et al.

It is certified that error appears in the above-identified patent and that said Letters Patent are hereby corrected as shown below:

Column 6, compound No. 13 - last column

"4.70" should be --4.72--.

Compound 20, column "C%" add--T.61,50--, under "th. 60,91".

Compound 20, col. "H%" add --5,98-- under "6,13".

Compound 20, col. "N%" add --4,60-- under "4,73".

Signed and Sealed this

Seventh Day of November 1978

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,086,352
DATED : April 25, 1978
INVENTOR(S) : Roland Yves Mauvernay et al.

It is certified that error appears in the above-identified patent and that said Letters Patent are hereby corrected as shown below:

On title page, [22] Filing date "Aug. 25, 1970"

should be --August 25, 1976--

Signed and Sealed this

Twenty-seventh Day of February 1979

[SEAL]

Attest:

RUTH C. MASON
Attesting Officer

DONALD W. BANNER
Commissioner of Patents and Trademarks